United States Patent [19]
McReynolds et al.

[11] Patent Number: 5,207,716

[45] Date of Patent: May 4, 1993

[54] SURGICAL HEAD SUPPORTING AND IMMOBILIZING APPARATUS

[76] Inventors: William U. McReynolds; William E. McReynolds; Ralph S. McReynolds, all of 2301 York St., Quincy, Ill. 62301

[21] Appl. No.: 851,184

[22] Filed: Mar. 13, 1992

[51] Int. Cl.⁵ .............................................. A61F 5/37
[52] U.S. Cl. ........................................ 128/870; 5/637
[58] Field of Search ............... 128/869, 870, 845, 846; 602/17, 18; 5/625, 628, 636, 637

[56] References Cited

U.S. PATENT DOCUMENTS

| | | | |
|---|---|---|---|
| 2,386,134 | 10/1945 | Mermis | 128/845 |
| 2,589,155 | 3/1952 | Smith | 5/637 |
| 2,651,302 | 9/1953 | Berry | 602/13 |
| 2,966,383 | 12/1960 | Boetcker | 5/637 |
| 3,957,262 | 5/1976 | McReynolds | 5/637 |
| 4,097,038 | 6/1978 | Jansen | 5/637 |
| 4,321,718 | 3/1982 | Chern | 5/637 |
| 4,390,011 | 6/1983 | Evans | 128/845 |
| 4,400,820 | 8/1983 | O'Dell | 128/845 |
| 4,545,572 | 10/1985 | Day | 5/637 |
| 4,979,519 | 12/1990 | Chavarria | 5/637 |
| 5,085,214 | 2/1992 | Barrett | 128/845 |

Primary Examiner—Robert A. Hafer
Assistant Examiner—Michael Brown
Attorney, Agent, or Firm—Lee, Mann, Smith, McWilliams, Sweeney & Ohlson

[57] ABSTRACT

An apparatus for supporting and immobilizing a head during ocular surgery or examination by a treating physician. A headrest is secured to a base support, the headrest having open sides and being shaped to engage a patient's head. A pair of immobilizing jaws engage the head from the side to hold the head in place. Repositionable arm platforms are provided for steadying the ocular physician's arms.

23 Claims, 3 Drawing Sheets

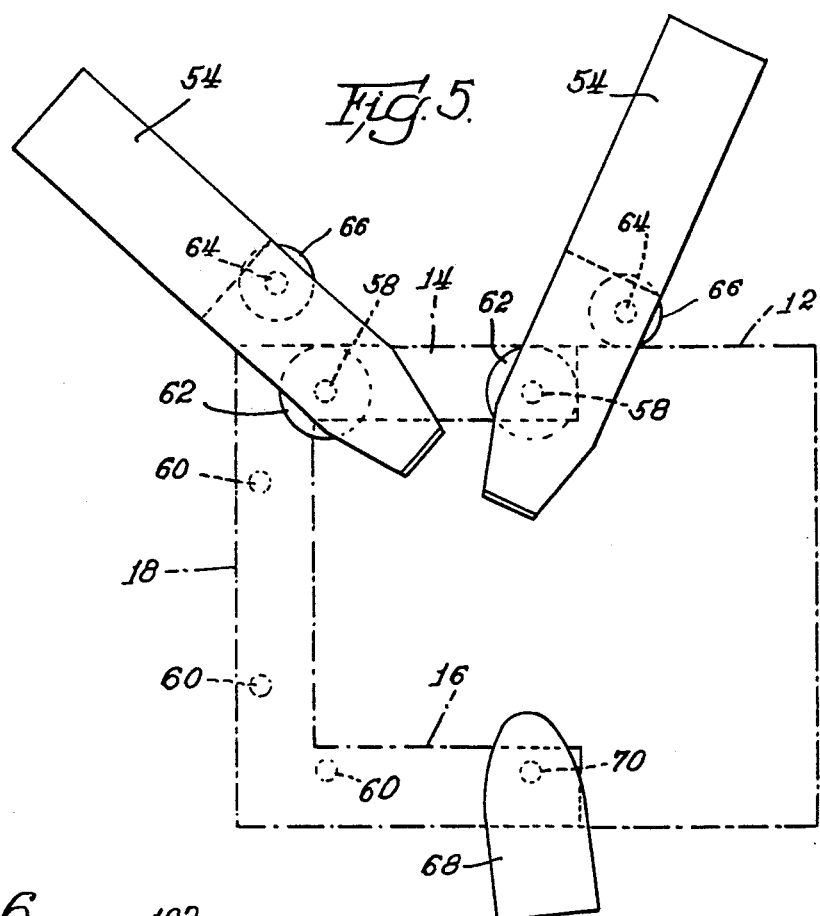
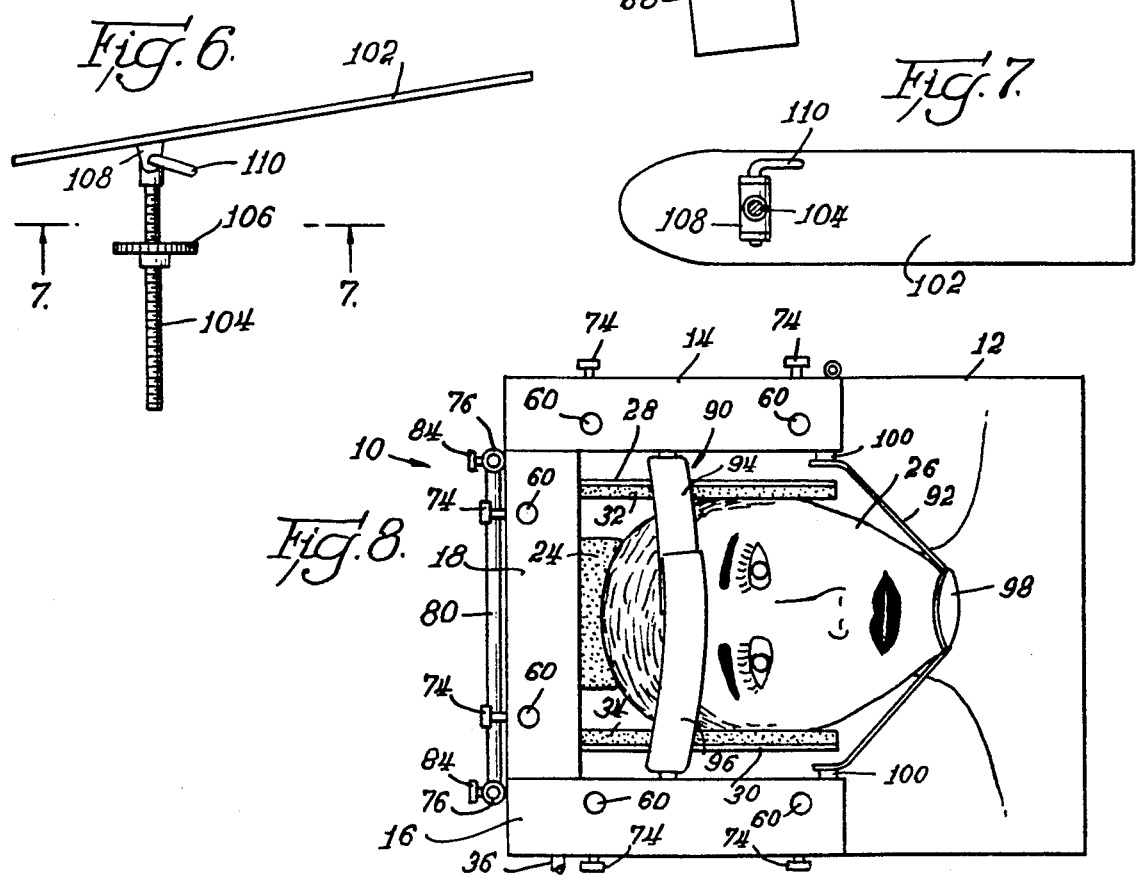

SURGICAL HEAD SUPPORTING AND IMMOBILIZING APPARATUS

BACKGROUND OF THE INVENTION

This invention relates to a head supporting and immobilizing apparatus, and in particular to an apparatus suitable for holding a patient's head at both a proper orientation and tightly during surgery or examination by a treating physician.

U.S. Pat. No. 3,957,262, detailing an invention developed by one of the inventors of the present application, is directed to a helmet-like device for supporting and immobilizing a patient's head during ocular surgery or treatment by a physician. As explained in that patent, it is important that the head be immobilized so that inadvertent motion does not interfere with the delicate surgical procedures being performed by a treating physician during surgery. Furthermore, it is important that the patient's head be held at a proper orientation to avoid undue strain and fatigue of the physician during the delicate surgical procedures, which can involve substantial periods of time.

U.S. Pat. Nos. 4,018,217 and 4,390,011 disclose armrests for a surgeon during ocular surgical procedures. However, the rests are generally for the hands, and no means of immobilizing the patient's head are provided.

SUMMARY OF THE INVENTION

The present invention is directed to a head supporting and immobilizing apparatus comprising a base support with a headrest portion secure thereto. The headrest portion is curved and shaped to engage both the back and the top of a patient's head when located in the head rest portion. A pair of head immobilizing jaws are carried by the base support, with one jaw being located on one side of the headrest portion and with a second jaw being located on the opposite side of the headrest portion. Means is provided for adjusting the jaws in unison toward and away from the headrest portion to clamp the patient's head in place. Means is also provided for steadying a portion of a physician's arm during delicate surgical procedures.

In accordance with the preferred form of the invention, the headrest portion is bi-concave shaped to comfortably fit the patient's head. Each jaw comprises a flat plate having a cushioning portion mounted thereon on a side facing the headrest portion. Upright side members are also provided, mounted on opposite sides of the base support, juxtaposed the jaws.

For adjustment of the jaws toward and away from the headrest portion, a threaded rod is provided, mounted for rotation in at least one of the side members. The threaded rod extends through an aperture in each jaw, with each aperture being provided with means threadedly engaging the rod. Preferably, the means threadedly engaging comprises a nut which is immobily secured to each jaw at the aperture. A hand crank is secured to one end of the rod for rotating the rod to advance or retreat the jaws.

For steadying the physician's arm or arms, at least one platform is provided, mounted on one of the side members. The platform includes a support shaft extending into a socket in the side member, and is provided with means for retaining the shaft. That means comprises an adjustable collar mounted on the shaft, and also a lock pin extending in the side member and engaging the shaft to prevent rotation of the shaft. The platform can be inclined for proper orientation of the physician's arm. Preferably, a series of the shaft-engaging sockets are provided so that one or more platforms can be mounted for the comfort and convenience of the attending physician.

The base support is generally flat, and normally extends horizontally. However, when a different orientation is required, means is provided for elevating one end of the base support. That elevating means includes at least one telescoping tube secured to one of the side members. Preferably, a pair of the tubes are provided, with each tube having a telescoping portion, and with an integral cross member connecting the telescoping portions. A lock pin engages each telescoping portion to retain the telescoping portion at any of a number of desired extended positions.

Means is also provided for tilting a patient's head when the patient's head is clamped within the apparatus of the invention. Preferably, that means comprises an inflatable bladder which is located beneath the neck of the patient. A compressible bulb is connected to the bladder for inflating or deflating the bladder both prior to, and during, surgical procedures.

While the nature of the invention holds the head quite satisfactorily, separate means is provided for securely holding the head when located in the apparatus. That means comprises a forehead strap and a chin strap, both of which are connected to the base support through the upright side members.

BRIEF DESCRIPTION OF THE DRAWINGS

The invention is described in greater detail in the following description of examples embodying the best mode of the invention, taken in conjunction with the drawing figures, in which:

FIG. 5 is a schematic top plan view of the invention showing another orientation of the armrests, with all other portions of the invention being removed or shown in phantom, FIG. 6 is an elevational view of a modified armrest according to the invention, FIG. 7 is a cross-sectional view of the bottom of the armrest of FIG. 6, taken along lines 7—7, and FIG. 8 is a top plan view of the invention, with the armrests and oxygen administration tube removed, and showing head restraining straps on a patient.

DESCRIPTION OF EXAMPLES EMBODYING THE BEST MODE OF THE INVENTION

Figure 1:
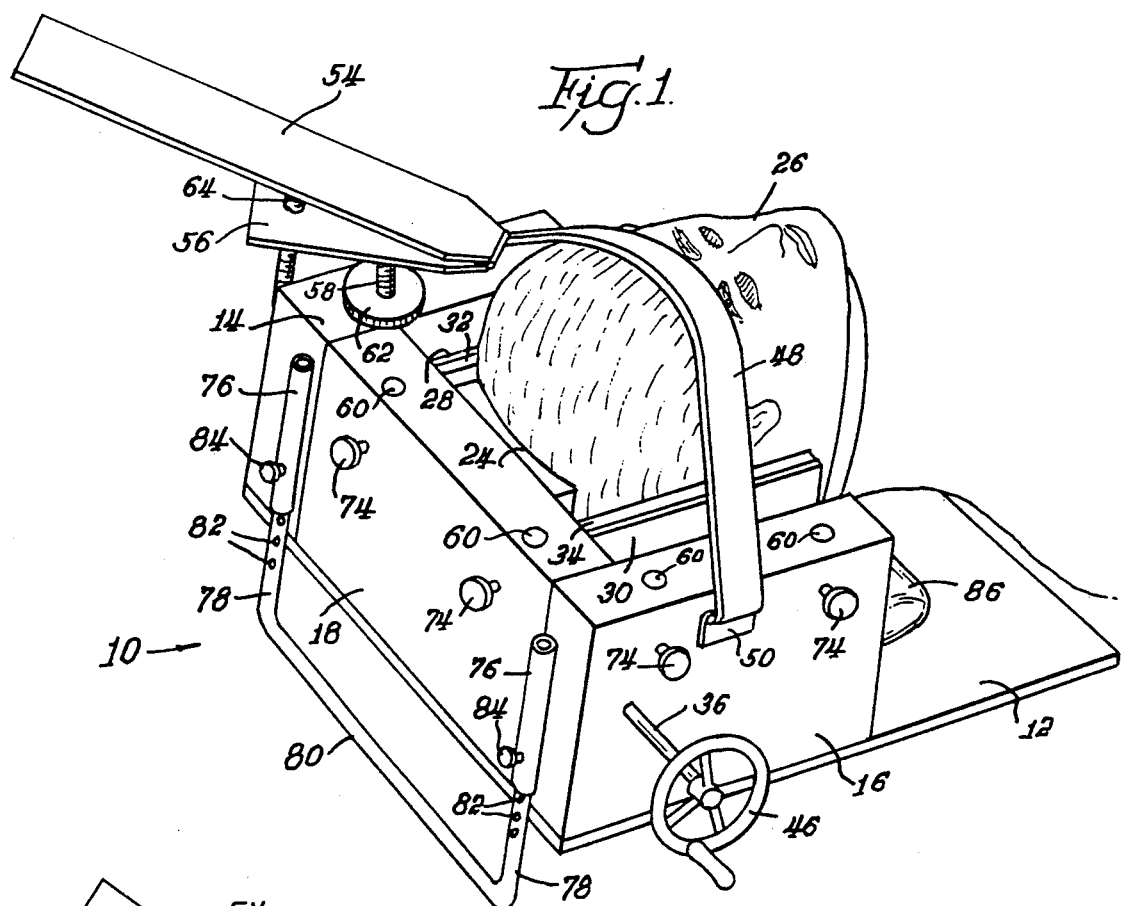
FIG. 1 is a perspective view of an apparatus according to the invention, with only one arm rest in place in order to illustrate detail, and with the forehead and chin straps omitted.
Figure 2:
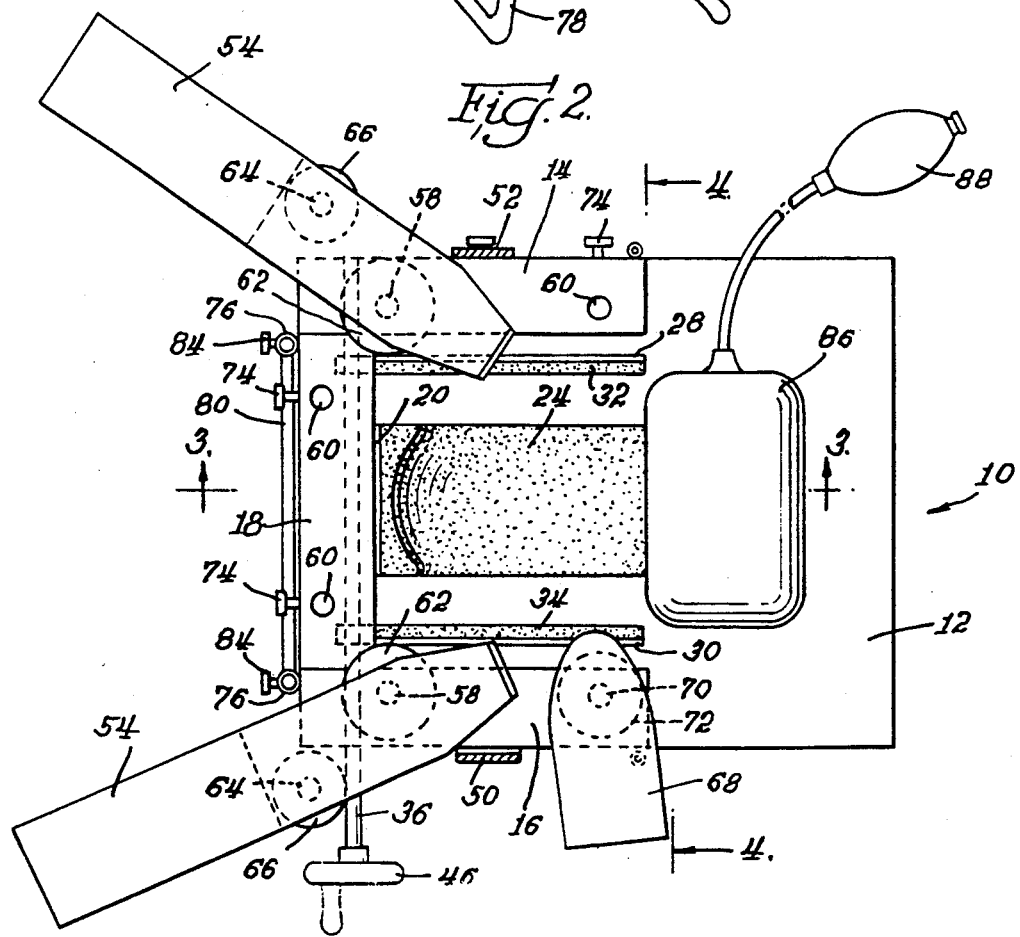
FIG. 2 is a top plan view of the apparatus according to the invention, with armrests shown in one possible orientation.

A head supporting and immobilizing apparatus according to the invention is shown generally at 10 in the drawing figures. The apparatus 10 consists of a base support 12, with a pair of upright side members 14 and 16 and an upright end member 18 mounted thereon. The members 14-18 may be hollow, and can be secured to the base support 12 in any conventional manner. The members 14-18 can be made of metal, such as aluminum, for sufficient rigidity, while the base support 12 can be made of plastic or any other suitable material which can be formed in a sufficiently large rectangular shape as shown in the drawing figures.

Figure 3:
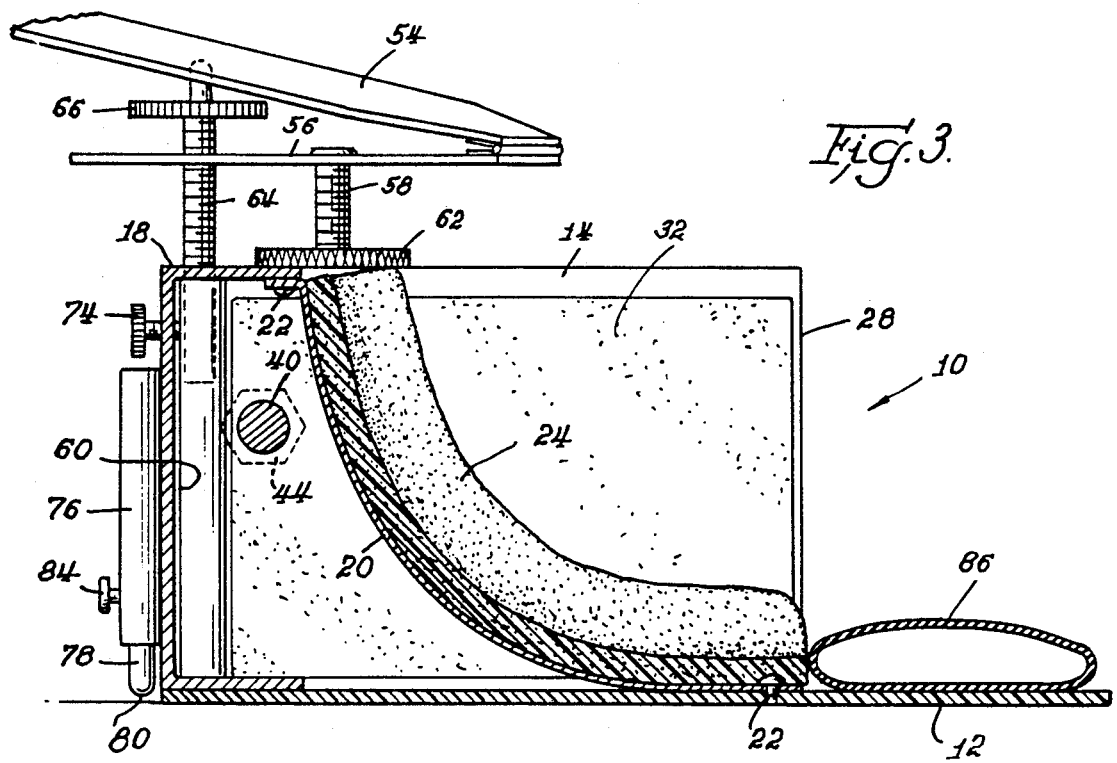
FIG. 3 is an enlarged cross-sectional view taken along lines 3—3 of FIG. 2.
Figure 4:
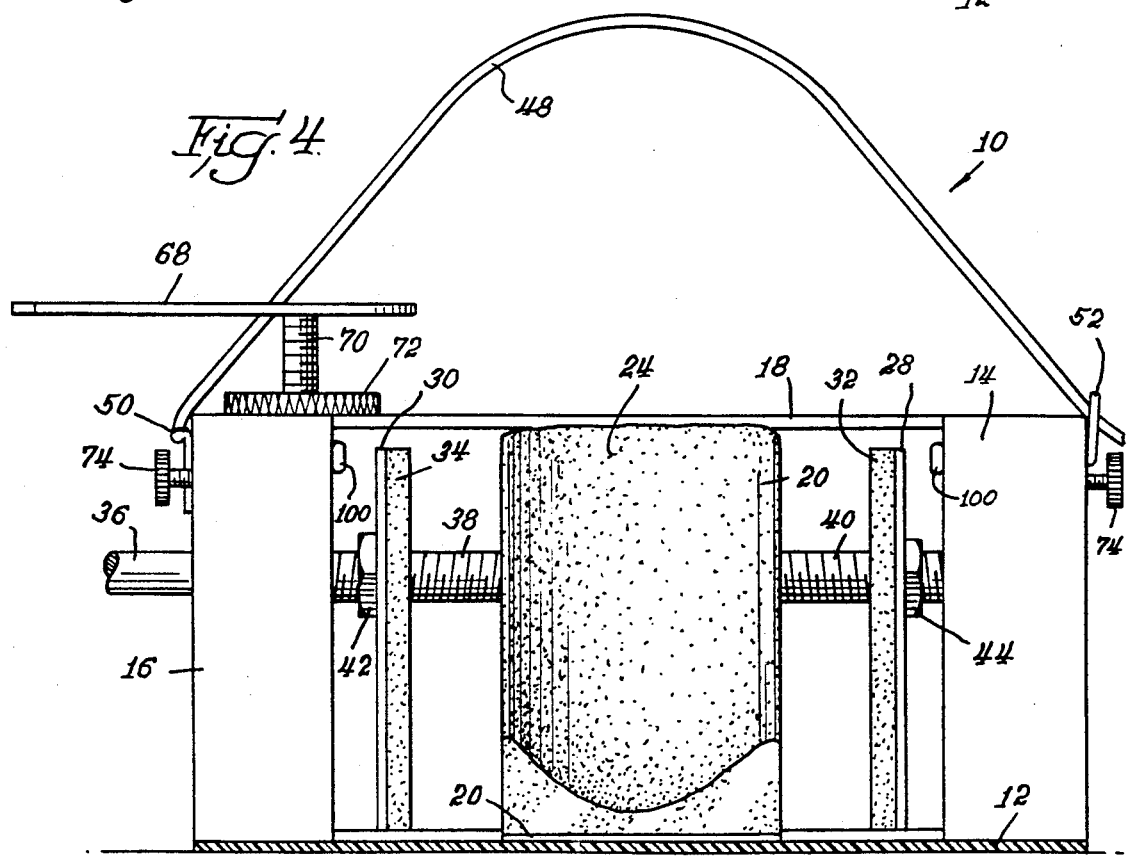
FIG. 4 is an enlarged cross-sectional and elevational view taken along lines 4—4 of FIG. 2, and showing an arched tube for administration of oxygen to a patient during surgery.

A headrest portion 20 is located centrally between the side members 14 and 16, being secured to both the base support 12 and the end member 18. As shown in FIG. 3, fasteners 22, such as screws, rivets or the like, may be used to fix the headrest portion 20 in place.

The headrest portion 20 is preferably bi-concave, and is formed of metal or plastic which can maintain the shape shown in the drawing figures. For comfort of the patient, the headrest portion 20 is lined with a soft material, such as a closed-cell foam pad 24, as illustrated.

The headrest portion 20 engages the top and back of the head 26 of a patient when supported within the apparatus 10. For immobilizing the patient's head, a pair of jaws 28 and 30 are carried by the base support 12, one jaw being located on each side of the headrest portion 20, and therefore on each side of the patient's head. The jaws 28 and 30 are juxtaposed the side members 14 and 16 as illustrated.

The jaws 28 and 30 are provided with respective cushions 32 and 34 for cushioning the head 26 of a patient. The jaws 28 and 30 extend within the end member 18, and are adjustable in unison toward and away from each other and the headrest portion 20 by means of a threaded rod 36. The rod 36 extends through conventional pivot bearings (not illustrated in detail) in each of the side members 14 and 16 so that the rod 36 can be freely rotated. The rod 36 also passes through apertures in each of the jaws 28 and 30. The portion 38 of the threaded rod 36 passing through the jaw 30 has a left hand thread, while the portion 40 of the rod 36 passing through the jaw 28 has a right hand thread. The portion 38 is engaged in a left hand-threaded nut 42, while the portion 40 is engaged in a right hand-threaded nut 44. The nuts 42 and 44 are secured to their respective jaws 30 and 28, such as by welding, so that rotation of the threaded rod 36 in one direction causes the jaws 28 and 30 to close toward the headrest portion 20, while rotation of the rod 36 in the opposite direction causes the jaws 28 and 30 to spread apart. The rod 36 is rotated by a hand crank 46.

Oxygen may need to be administered to a patient during certain ocular surgery. The apparatus 10 is provided with an arched, perforated tube 48 which is hinged at one end 50 to the side member 16 and which passes through an appropriate bracket 52 on the opposite side member 14. Oxygen is supplied to the tube 48 from a source (not illustrated), and the tube 48 is sufficiently rigid to support surgical drapes above a patient during surgical procedures.

Ocular surgical procedures are delicate, requiring great precision of the attending physician. To support and steady a physician's arm, the apparatus 10 includes one or more support platforms 54. Each platform 54 is hinged to an intermediate, horizontal platform 56. A threaded support shaft 58 is secured to and extends beneath the horizontal platform 56, and is engaged in one of a series of vertical sockets 60. The sockets 60 may each comprise a vertical tube in the side members 14 and 16 and end member 18 to permit the physician to reposition one or more support platforms 54 as required and desired for treating of an ocular surgery patient.

The elevation of each of the platforms 54 above the members 14-18 is determined by an adjustable collar 62 engaged on the threaded support shaft 58. The collar 62 bears upon the top of the member 14-18 in which the shaft 58 is inserted, thus determining the elevation of the support platform 54.

The inclination of the support platform 54 is controlled by means of a second shaft 64 that is threadedly engaged in an aperture in the horizontal platform 56. The second shaft 64 bears on the underside of the support platform 54 and, by rotation of the shaft 64 by means of an annular thumb control 66, the inclination of the platform 54 can be altered as desired.

The platform 54 is sufficient in length to support all or the great majority of the forearm of a physician. For physicians not desiring a full length platform, or for assistants who do not require support of the forearm, an assistant's platform 68 is provided. The assistant's platform 68 does not have an adjustable inclination, and is mounted above one of the members 14-18 by means of a support shaft 70 threadedly engaged within a collar 72 and extending into one of the sockets 60. The collars bears atop one of the members 14-18 in the same manner as the collar 62 of the support platforms 54, and the elevation of the assistant's platform 68 is adjusted in the same manner. The assistant's platform 68 can be located in any of the sockets 60, in the same fashion as the support platforms 54.

Once the support shafts 58 or 70 are inserted in one of the desired sockets 60, the shafts can be locked in place by means of set screws 74, one of which is associated with each of the sockets 60. By turning of a set screw 74 to cause it to bear against a support shaft, the support shaft, and therefore the associated platform, is locked in place.

Normally, the base support 12 is disposed horizontally when a patient is held by the apparatus 10. On occasion, however, the attending physician may desire to elevate the head end of the apparatus 10. To this end, the apparatus 10 is provided with a telescoping support comprising a pair of tubes 76 affixed to the side members 14 and 16. A telescoping portion 78 extends from each of the tubes 76, with an integral cross member 80 interconnecting the telescoping portions 78. Each of the telescoping tube portions 78 has a series of holes 82 therein which are engaged by a spring-loaded pin 84. Thus, the elevation of the head end of the base support 12 can be changed by adjusting the extent to which the telescoping portions 78 extend from the tubes 76.

It is also important to tilt the patient's head 26 when captured between the jaws 28 and 30. An inflatable air bladder 86 is secured to the base support 12 beneath the patient's neck, and is inflated by a compressible bulb 88 in a conventional fashion. The physician can use the bulb 88 to inflate or deflate the air bladder 86 as required during the surgical procedure.

The contoured headrest portion 20 in combination with the adjustable jaws 28 and 30 serve to hold a patient's head quite securely. For added security of positioning of the patient's head, the apparatus 10 is provided with a forehead strap 90 and a chin strap 92. The forehead strap 90 is preferably comprised of strap portions 94 and 96 which are affixed to the respective side members 14 and 16, and which are fastened to one another by means of a hook-and-loop fastener, such as a Velcro brand fastener. The chin strap 92 may include a chin cup 98, and is fastened to the side members 14 and 16 by snaps 100.

An alternative form of support platform 102 is shown in FIGS. 6 and 7. The support platform 102 is secured to a support shaft 104 which may be inserted in one of the sockets 60. A collar 106 is threadedly engaged on the shaft 104 for adjusting the elevation of the support platform 102 in precisely the manner the platforms 54 are adjusted.

A conventional cam lock 108 connects the shaft 104 to the underside of the support platform 102. The cam lock 108 is operated by a lever arm 110, and when the lever arm 110 is rotated to loosen the cam lock 108, the support platform 102 may be tilted as desired. The lever arm 110 is then rotated in the opposite direction to fix the cam lock 108 in place to lock the platform 102 at a desired inclination.

The apparatus 10 is used in a straightforward manner. With the straps 90 and 92 removed or opened, and the jaws 28 and 30 sufficiently spread, the head 26 of a patient is placed on the headrest portion 20, and the jaws 28 and 30 are then closed by rotation of the threaded rod 36. Once the head is held comfortably in place, the straps 90 and 92 are replaced. If the head is to be tilted at all, the air bladder 86 is inflated as needed. Also, if the base support 12 is to be inclined at all, the telescoping portions 78 are extended as needed. The physician then inserts one or more of the support platforms 54 or 102 in the sockets 60, rotates the platforms as needed, elevates them as desired, and locks them in place. The assistant's platform 68 is also installed, if used. Surgical drapes can then be placed about the patient's head, with the arched tube 48 supporting them above the patient's head.

Due to the series of sockets 60, the support platforms 54 or 102 can be oriented and located about the patient's head as desired by the physician for maximum versatility and utility. The air bladder 86 can be inflated or deflated during the surgical procedure to fine tune the orientation of the patient's head for the maximum accessibility to the physician.

Various changes can be made to the invention without departing from the spirit thereof or scope of the following claims.

What is claimed is:

1. A head supporting and immobilizing apparatus, comprising
   a. a base support,
   b. a headrest portion secured to said base support, said headrest portion having open sides, and being curved and shaped to engage only the back and top of a head when located in said headrest portion, with the sides of the head not being engaged by the headrest portion,
   c. a pair of head immobilizing jaws carried by said base support, one jaw being located on one side of said headrest portion and being engageable with one side of a head, and a second jaw being located on an opposite side of said headrest portion and being engageable with an opposite side of a head,
   d. means for adjusting said jaws in unison toward and away from said headrest portion for engagement with the sides of a head, and
   e. means for steadying a portion of a physician's arm.

2. A head supporting and immobilizing apparatus according to claim 1 in which said headrest portion is bi-concave shaped.

3. A head supporting and immobilizing apparatus according to claim 1 in which each jaw comprises a flat plate having a cushioning portion mounted thereon on a side facing said headrest portion.

4. A head supporting and immobilizing apparatus according to claim 1 including upright side members mounted on opposite sides of said base support juxtaposed said jaws.

5. A head supporting and immobilizing apparatus according to claim 4 in which said adjusting means comprises a threaded rod mounted for rotation in at least one of said side members and an aperture in each jaw through which said rod passes, each aperture including means threadedly engaging said rod.

6. A head supporting and immobilizing apparatus according to claim 5 in which said means threadedly engaging comprises a nut secured to each jaw at said aperture.

7. A head supporting and immobilizing apparatus according to claim 5 including a hand crank secured to one end of said rod for rotating said rod.

8. A head supporting and immobilizing apparatus according to claim 4 in which said steadying means comprises at least one platform mounted on a side member.

9. A head supporting and immobilizing apparatus according to claim 8 in which said platform includes a support shaft extending into a socket in said side member, and including means for retaining said shaft.

10. A head supporting and immobilizing apparatus according to claim 9 in which said retaining means comprises an adjustable collar mounted on said shaft.

11. A head supporting and immobilizing apparatus according to claim 10 in which said retaining means further comprises a lock pin extending in said side member and engaging said shaft.

12. A head supporting and immobilizing apparatus according to claim 9 including a plurality of said sockets.

13. A head supporting and immobilizing apparatus according to claim 8 including means for inclining said platform.

14. A head supporting and immobilizing apparatus according to claim 4 including means for elevating one end of said base support.

15. A head supporting and immobilizing apparatus according to claim 14 in which said elevating means comprises at least one telescoping tube vertically secured to a said side member.

16. A head supporting and immobilizing apparatus according to claim 15 including a pair of said tubes, each said tube having a telescoping portion, and a cross member connecting said telescoping portions.

17. A head supporting and immobilizing apparatus according to claim 15 including a lock pin engaging a telescoping portion of said tube to retain said telescoping portion at an extended position.

18. A head supporting and immobilizing apparatus according to claim 1 including means for tilting a head when located within said apparatus.

19. A head supporting and immobilizing apparatus according to claim 18 in which said means for tilting comprises an inflatable bladder.

20. A head supporting and immobilizing apparatus according to claim 19 including a compressible bulb connected to said bladder for inflating said bladder.

21. A head supporting and immobilizing apparatus according to claim 1 including means for holding a head when located within said apparatus.

22. A head supporting and immobilizing apparatus according to claim 21 in which said holding means comprises a forehead strap secured to said base support.

23. A head supporting and immobilizing apparatus according to claim 22 in which said holding means further comprises a chin strap secured to said base support.

* * * * *